United States Patent [19]

Walker et al.

[11] 3,952,039

[45] Apr. 20, 1976

[54] CATALYTIC PROCESS FOR POLYHYDRIC ALCOHOLS AND DERIVATIVES

[75] Inventors: Wellington E. Walker, Charleston; David R. Bryant; Earle S. Brown, Jr., both of South Charleston, all of W. Va.

[73] Assignee: Union Carbide Corporation, New York, N.Y.

[22] Filed: July 12, 1974

[21] Appl. No.: 488,141

[52] U.S. Cl. .................... 260/449 R; 252/431 R; 252/431 N; 252/431 L; 252/431 P; 252/443; 260/449 L; 260/449.5; 260/485 G; 260/488 J
[51] Int. Cl.² .......................................... C07C 27/06
[58] Field of Search ......... 260/449 R, 449 L, 449.5; 252/431 R, 431 N, 431 P, 431 L, 443

[56] References Cited
UNITED STATES PATENTS

| | | | |
|---|---|---|---|
| 2,692,274 | 10/1954 | Kolbel et al. .................... | 260/449 L |
| 3,081,357 | 3/1963 | Alderson et al. .................... | 252/443 |
| 3,576,881 | 6/1971 | Senn .............................. | 260/604 HF |
| 3,725,534 | 4/1973 | Reisch ...................... | 260/604 HF X |
| 3,833,634 | 9/1974 | Pruett et al. .................... | 260/449 R |

FOREIGN PATENTS OR APPLICATIONS

| | | | |
|---|---|---|---|
| 793,086 | 6/1973 | Belgium .......................... | 260/449 |

OTHER PUBLICATIONS

Martinengo et al., Gazz, 102 (1972), 344–354.

*Primary Examiner*—Howard T. Mars
*Attorney, Agent, or Firm*—George A. Skoler

[57] ABSTRACT

This invention relates to the manufacture of such valuable chemicals as polyhydric alcohols, their ether and ester derivatives, oligomers of such alcohols and monohydric alcohols and their ether and ester derivatives by reacting oxides of carbon and hydrogen in the presence of an alkali metal cation and a rhodium carbonyl complex provided to the reaction as a rhodium carbonyl cluster anion which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$ and said cation is present in the reaction mixture in about 0.5 to about 1.5 atoms of cation per every six rhodium atoms in the cluster.

12 Claims, No Drawings

CATALYTIC PROCESS FOR POLYHYDRIC ALCOHOLS AND DERIVATIVES

This invention is concerned with an improved process for the manufacture of polyhydric alcohols, their ether and ester derivatives, and oligomers of such alcohols. This invention also produces monohydric alcohols such as methanol, and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

It is known that monofunctional compounds such as methanol can be obtained by reaction between carbon monoxide and hydrogen at elevated pressures, e.g., up to about 1000 atmospheres, and temperatures ranging from 250°C to 500°C, using mixtures of copper, chromium and zinc oxides as the catalyst therefor. It is disclosed in U.S. Pat. No. 2,451,333 that polyhydroxyl compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British 655,237, published July 11, 1951, there is disclosed the reaction between carbon monoxide and hydrogen at elevated pressures and temperatures up to 400°C, using certain hydrogenation catalysts as exemplified by cobalt-containing compounds. U.S. Pat. Nos. 2,534,018; 2,570,792 and 2,636,046 are substantially similar in disclosure to the above said British patent. The only catalysts employed in the numbered examples of said U.S. Pat. 2,636,046 are those which contain cobalt.

It is also well-known that nickel is predominantly a catalyst for synthesis and for reforming methane according to the reaction

$$CO + 3H_2 \rightleftarrows CH_4 + H_2O$$

which proceeds from left to right at temperatures below about 500°C and in the opposite direction at higher temperatures; see Kirk-Othmer, Encyclopedia of Chemical Technology, Second Edition, Volume 4, pp. 452–453, John Wiley and Sons, New York (1964).

In copending application Ser. No. 219,130, filed Jan. 19, 1972, now U.S. Pat. No. 3,833,634, and Belgium Patent No. 793,086, published June 20, 1973, there is disclosed a process for the preparation of polyhydric alcohols by contacting a mixture of carbon monoxide and hydrogen with a catalytic amount of rhodium in complex combination with carbon monoxide.

Copending application, Ser. No. 462,109, filed Apr. 19, 1974, characterizes an improvement on the invention of Ser. No. 219,130. There is disclosed in Ser. No. 462,109 a process for manufacturing polyhydric alcohols, their ether and ester derivatives, oligomers of such alcohols and monohydric alcohols and their ether and ester derivatives by reacting the oxides of carbon and hydrogen in the presence of a rhodium carbonyl complex which is provided to the reaction as a rhodium carbonyl cluster which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$ at a pressure of at least about 500 pounds per square inch, in associated with a counter-ion. Suitable counter-ions for the cluster are a variety of metals and organic compounds. Included as metal counter-ions are the alkali metal cations.

This invention is directed to an improvement in the process of Ser. No. 462,109 for making polyhydric aliphatic alcohols and their ether, ester, and oligimer derivatives, such as alkane polyols, most specifically, alkane diols and triols, containing 2 or 3 carbon atoms, their ether, ester and oligimer derivatives.

As with the process of Ser. No. 462,109, a byproduct of this invention is the manufacture of the lesser valuable, but valuable nevertheless, monohydric alkanols such as methanol, ethanol, and propanol, and their ether and ester derivatives. The products of this invention contain carbon, hydrogen and oxygen.

It has been found that greater yields of polyhydric alcohols, their ether and ester derivatives, oligimers of such alcohols and monohydric alcohols and their ether and ester derivatives are obtainable at significantly lower operating temperatures and pressures when, in reacting the oxides of carbon and hydrogen in the presence of an alkali metal cation and a rhodium carbonyl complex, the alkali metal cation is present in the reaction mixture in about 0.5 to 1.5 atoms of cation per six atoms of rhodium charged to the reactor. The complex is provided to the reaction as a rhodium carbonyl cluster which possesses an infrared spectrum which exhibits three intense wavelength bands between about plus and minus 10 cm$^{-1}$ of about 1868 cm$^{-1}$, and about 1838 cm$^{-1}$, and about 1785 cm$^{-1}$.

The rhodium carbonyl cluster of this invention exhibits the above infrared spectrum either during the reaction or at a temperature and/or pressure below that at which the reaction is effected. In both instances, the catalytic effect is achieved suggesting that the characterized rhodium clusters are always present.

P. Chini, in a review article entitled "The Closed Metal Carbonyl Clusters" published in Reviews (1968), Inorganica Chemica Acta, pp. 30–50, states that a metal cluster compound is "a finite group of metal atoms which are held together entirely, mainly, or at least to a significant extent, by bonds directly between the metal atoms even though some non-metal atoms may be associated intimately with the cluster". The rhodium carbonyl cluster compounds of this invention contain rhodium bonded to rhodium or rhodium bonded to another metal, such as cobalt, and/or iridium. The preferable rhodium carbonyl cluster compounds of this invention are those which contain rhodium-rhodium bonds. These compounds desirably contain carbon and oxygen in the form of carbonyl (—C—O), in which the carbonyl may be "terminal", "edge bridging", and/or "face bridging". They may also contain hydrogen and carbon in forms other than carbonyl. The following are illustrative of what is believed to be the structure of two distinct rhodium carbonyl cluster ions and both are suitable for use in this invention:

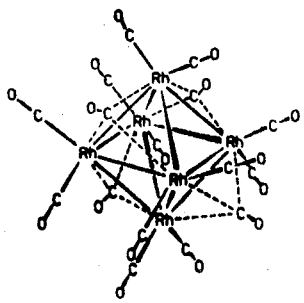

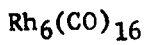
Rh$_6$(CO)$_{16}$

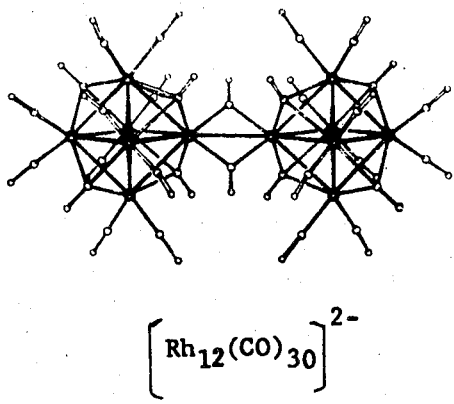

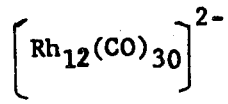
$[Rh_{12}(CO)_{30}]^{2-}$

The structures of the rhodium carbonyl clusters may be ascertained by X-ray crystal diffraction, nuclear magnetic resonance spectra, NMR, or infrared spectra as disclosed in the article entitled "synthesis and Properties of the Derivatives of the [Rh$_{12}$(CO)$_{30}$]$^{2-}$ Anion" by P. Chini and S. Martinengo; appearing in Inorganica Chemica Acta, 3:2, pp. 299–302, June (1969). Of particular analytical utility in the present invention is the use of infrared spectroscopy which allows for qualitative and what is presently believed to be a quantitative characterization of the particular rhodium carbonyl cluster present during the operation of the process of the present invention.

Rhodium carbonyl cluster ions which possess the infrared spectrum characcterized previously, function in association with oxides of carbon and hydrogen, as herein defined, to produce the polyhydric alcohols, etc. The exact mechanism by which the cluster compounds act to catalyze the reaction is not fully appreciated at this time. It is believed that the reaction is dependent upon the existence of the following equilibria:

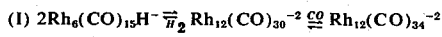

In practicing the present invention the rhodium carbonyl cluster catalyzed reaction of carbon monoxide and hydrogen is carried out in the presence of about 0.5 to about 1.5 atoms, preferably in about 0.75 to about 1.5 atoms, preferably in about 0.75 to about 1.25 atoms, and more preferably in about 1 atom of alkali metal cation per every six atoms of rhodium also present in the reaction mixture. Particularly suitable alkali metal cations are the ions of sodium, potassium, lithium, rubidium, cesium or mixtures thereof. The preferred alkali metal cation is cesium.

The precise role of the alkali metal cation in the reaction of carbon monoxide and hydrogen catalyzed by the rhodium carbonyl clusters to produce polyhydric alcohols is not clearly understood. The reaction is believed to involve the reaction of carbon monoxide with the active catalytic species to form a radical of CO which may or may not require the addition of another radical of CO prior to hydrogenation to form the polyhydric alcohol or methanol. Infrared analysis shows that under reaction conditions which favor the production of polyhydric alcohols, the characteristic 3 band pattern of the [Rh$_{12}$(CO)$_{34}$]$^{2-}$ cluster is present; while under conditions which favor the production of methanol, only the single band pattern about 1900 cm$^{-1}$, of the monomeric Rh(CO)$_4^-$ anion is dominant and the aforementioned 3 band pattern is missing or minimized in intensity.

The use of about 0.5 to about 1.5 atoms of alkali metal cation for every six atoms of rhodium present in the reaction mixture allows for the production of polyhydric alcohols at lower operating pressures with no reduction of product yield for a given set of reaction conditions. When the amount of alkali metal cation in the rection is greater or less than this amount, the productivity and efficiency of reaction to polyhydric alcohol is significantly reduced and the reaction conditions required to achieve results remotely comparable are much more stringent and costly.

In view of the fact that the alkali metal cation does not enter into the reaction, and it has not been clearly established to be necessary for catalyst formation or stability, the presence of this select amount of the cation for optimum catalysis when the counter-ion is an alkali metal, is not clearly understood. In terms of the results achieved, it would appear that such select amount of the alkali metal functions in a manner which may reduce factors which inhibit the aforementioned CO radical formation.

The rhodium carbonyl complex is, as characterized above, a rhodium containing compound in which the rhodium values are complexed with CO.

In these terms "complex" means a coordination compound formed by the union of one or more electronically rich organic molecules or atoms capable of independent existence with one or more electronically poor molecules or atoms, each of which is also capable of independent existence. These organic rhodium cluster complexes are derived from the association of organic ligands or organic counter-ions with rhodium carbonyl solutions.

Organic ligands which are suitable in the practice of the invention contain at least one nitrogen atom (hereinafter call Lewis base nitrogen atom) and/or at least one oxygen atom (hereinafter called Lewis base oxygen atom), said atoms possessing a pair of electrons available or the formation of coordinate bonds with rhodium. Suitably, the organic ligand contains at least two Lewis base nitrogen atoms, or at lest two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium per se a chelate structure. In suitable embodiments the organic ligands contain from 1 and upwards to 4 Lewis base atoms, preferably from 1 to 3 such atoms, and most preferably 1 or 2 Lewis base atoms. These organic ligands are said to be multidentate or polydentate, that is to say, such ligands are bidentate, tridentate, or quadridentate, depending on whether 2, 3, or 4 Lewis base atoms are involved in the formation of chelate structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino (—N—), nitrilo (N ), etc. Desirably, the Lewis base nitrogen atoms are in the form of imino nitrogen and/or amino nitrogen. The oxygen atoms can be in the form of groups such as hydroxyl (aliphatic or phenolic), carboxyl

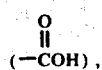

carbonyloxy

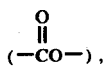

oxy (—O—), carbonyl

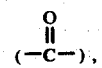

etc., all of said groups containing Lewis base oxygen atoms. In this respect, it is the "hydroxyl" oxygen in the

group and the "oxy" oxygen in the

-continued

group that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N-tetraisobutylmethylenediamine, piperazine, N-methylpiperazine, N-ethylpiperazine, 2-methyl-N-methylpiperazine, 2,2'-dipyridyl, methylsubstituted 2,2-'dipyridyl, ethyl-substituted 2,2'-dipyridyl, 1,4-diazabicyclo [2.2.2] octane, methylsubstituted 1,4-diazabicyclo [2.2.2] octaine, purine, 2-amino-pyridine, 2-(dimethylamino) pyridine, 1,10-phenan-throline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, digylcolic acid, thiodiglycolic acid, diether ether, tetrahydrofuran, dioxane, tetrahydropyran, pyrocatechol, citric acid, 2-methoxyethanol, 2ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenezene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hyroxyethyl) iminodiacetic acid, ethylenediaminetetraacetic acid, 2,6-dicarboxypyridine, 8-hyroxyquinoline, 2-carboxyquinoline, cyclohexane-1,2-diamine-N,N,N',N'-tetraacetic acid, the tetramethyl ester of ethylenediaminetetraacetic acid, and the like.

Other organic counter-ions are formed by ionic association with the rhodium carbonyl cluster ions. They are from organic compounds which possess Lewis base nitrogen atoms and typically are composed of carbon, hydrogen and nitrogen. Illustrative of such compounds are, e.g., piperidine, 2-methylpiperidine, 3-methylpiperidine, pyridine, 2-methylpyridine, 4-ethylpiperidine, triethylamine, benzyltrimethyl ammonium acetate and formate, tri-n-butylamine, dibutylamine, methylamine, dodecylamine, morpholine, aniline, benzylamine, octadecylamine, naphthylamine, cyclohexylamine, and the like.

In the practice of the present invention a normally liquid organic solvent is employed in an amount sufficient to maintain a homogeneous reaction mixture containing the cluster and the alkali metal cation. Illustrative of the solvents which are generally suitable in the practice of the present invention include, for example, saturated and aromatic hydrocarbons, e.g., hexane, octane, dodecane, naptha, decalin, tetrahydronaphthalene, kerosene, mineral oil, cyclohexane, cycloheptane, alkylcycloalkane, benzene, toluene, xylene, naphthalene, alkylnaphthalene, etc; ethers such as tetrahydrofuran, tetrahydropyran, diethyl ether, 1,2-dimethoxybenzene, 1,2-ethoxybenzene, the mono- and dialkyl ethers of alkylene glycols and polyalkylene glycols, such as ethylene glycol, of propylene glycol, of butylene glycol, of diethylene glycol, of dipropylene glycol, of triethylene glycol, of tetraethylene glycol of pentaethylene glycol, of dibutylene glycol, of oxyethyleneoxypropylene glycol, etc., preferably, those in which the alkylene group contains 2 carbon atoms in the divalent moeity, such as, ethylene and 1,2-propylene; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethyl-hexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride, etc.; lactones such as γ-butyrolactone and valerolactone, etc.; and others γ-butyrolactone and the mono and dialkyleters of triethylene and tetraethylene glycol are the preferred solvents in the practice of the present invention.

It should be noted that the use of reactive solvents in the practice of desirable embodiments of this invention can give rise to a range of useful products. For instance, the mono- and diacetate esters of ethylene glycol can be obtained by using acetic acid as the solvent in the reaction medium. The use of alkanols, e.g., methanol and ethanol, can result in the monoalkyl ethers of ehtylene glycol. ethylene In one of the embodiments of the present invention, the metal cation may be provided to the reaction mixture in the form of its alkali metal salt. Suitable alkali metal salts useful in the present invention include the alkali metal halides, for instancce the fluoride, chloride, bromide and iodide salts and the alkali metal carboxylates, such as formate, acetate, pripionate, and butyrate salts. Other alkali metal salts useful in the present invention include compounds of the general formula:

M—O—R wherein M is an alkali metal selected from the group of sodium, potassium, lithium, rubidium, and cesium and R can represent hydrogen; an alkyl group, such as methyl, ethyl, isopropyl, 2-ethylhexyl and the like; or an aryl group such as phenyl, tolyl, napthyl, and the like; or a functionally substituted alkyl such as ethoxymethyl, ethoxyethyl, phenoxyethyl, and the like, or a cyclic or bicyclic hydrocarbon such as cyclohexyl, cyclopentyl, bicycloheptyl and the like; or a heterocyclic group, such as pyridinyl, quinolinyl, and the like.

The preferred alkali metal salts useful in the present invention are the formate, acetate, 2-pyridinolate and fluoride salts of cesium.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, or rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. No particular advantages at the relatively high concentrations of rhodium are manifest. Depending on various factors such as the cation of choice, the partial pressures of oxides of carbon and hydrogen, the total operative pressure of the system, the operative temperature, the choice of the normally-liquid organic solvent, and other considerations, a catalyst concentration of from about $1 \times 10^{-5}$ to about $1 \times 10^{-1}$ weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100° C. and upwards to approximately 375°C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Suitable operative temperatures are between about 150°C. to about 300°C., preferably from about 190°C. to about 275°C., and more preferably about 190°C to about 240°C.

The equilibrium reaction for forming ethylene glycol is:

$$2\ CO + 3H_2 \rightleftharpoons HOCH_2CH_2OH$$

At relatively high temperatures the equilibrium increasingly favors the left hand side of the equation. In the practice of the present invention, to drive the reaction to the formation of a fixed increased quantity of ethylene glycol, lower partial pressures of carbon monoxide and hydrogen are required than those taught by the prior art.

This novel process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. However, at pressures greater than about 15,000 psia no improvement in the productivity of polyhydric alcohol can be attributed to the presence of the alkali metal cation in the select amount. This nonbeneficial effect of the cation at high pressures is believed due to the overriding effect the increased pressure of carbon monoxide has on the stability of the rhodium carbonyl cluster. A suitable pressure range for effecting the novel process is from about 1000 psia to about 15,000 psia, preferably about 2000 psia to about 12,000 psia, and more preferably about 6,000 psia to about 10,000 psia. The pressures referred to above represent the total pressure of hydrogen and oxides of carbon.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reactor. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active rhodium species, if necessary. Fresh rhodium catalyst can be intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances as well as the cation forming substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide, ($Rh_2O_3$), tetrarhodium dodecarbonyl, dirhodium octacarbonyl, hexarhodium hexadecacarbonyl $Rh_6(CO)_{16}$), rhodium (II) formate, rhodium (II) acetate, rhodium (II) propionate, rhodium (II) butyrate, rhodium (II) valerate, rhodium (III) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), tris (hexane-2,4 -dionato)rhodium (III), tris(heptane-2,4-dionato)rhodium(III), tris (1-phenylbutane-1,3-dionato)rhodium(III), tris(3-methylpentane-2,4-dionato)rhodium-(III) and tris(1-cyclohexylbutane-1,3-dionato)rhodium(III).

The preparation of rhodium carbonyl cluster compounds is conveniently carried out in a diluent or mixture of diluents, e.g., benzene, Tetrarhodium dodecarbonyl, though of limited solubility, can be added to the diluent in a finely divided form. Any of several of the rhodium-containing compounds illustrated previously can be employed in lieu of $Rh_4(CO)_{12}$. Organic ligands such as 2-hydroxypyridine or other counter-ion forming compounds can also be added thereto. The cluster forming reaction can be effected under a carbon monoxide pressure, with or without $H_2$, of about 1 to about 15 atmospheres, and higher, using a temperature of about 30°C. to about 100°C., for a period of time ranging from minutes to a few days, generally from about 30 minutes to about 24 hours. The resulting rhodium cluster compound contained in the organic diluent is catalytically active in this process. The compound contains rhodium in clustered combination with carbon monoxide and the aforementioned select amount of alkali metal cation of choice.

Other suitable methods for preforming the rhodium carbonyl cluster alkali metal salts useful in the present invention are disclosed in an article entitled "Synthesis and Properties of derivatives of the $[Rh_{12}(CO)_{30}]^{2-}$ Anion", by Chini et al appearing in *Inorg. Chem. Acta*, 3(2), pp. 299–302,(1969).

The equipment arrangement and procedure which provides the capability for determining the existence of rhodium carbonyl clusters having the aforedefined infrared spectrum characteristics, during the course of the manufacture of polyhydric alcohols from carbon monoxide and hydrogen, pursuant to this invention, are disclosed and schematically depicted in U.S. Pat. application, Ser. No. 462,109, filed Apr. 18, 1974, which is a continuation-in-part of application Ser. No. 371,350, filed June 19, 1973, which in turn is a continuation-in-part of application Ser. No. 219,130, filed Jan. 19, 1972, which in turn is a continuation-in-part of abandoned application Ser. No. 210,538, filed Dec. 21, 1971, the disclosures of which are incorporated herein by reference.

A particularly desirable infrared cell construction is described in copending U.S. Pat. application, Ser. No. 451,437, filed Mar. 15, 1974, which is a continuation-in-part application of abandoned U.S. application, Ser. No. 371,352, filed June 19, 1973, and their disclosures of preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction.

The following examples are nearly illustrative and are not presented as a definition of the limits of the invention.

The following procedure was used for examples 1 through 9 listed in Table I.

A 150 ml. capacity stainless steel reactor capable of withstanding pressures up to 7,000 atmospheres was charged with a premix of 75 cubic centimeters (cc) of the dimethylether of tetraethylene glycol (tetraglyme) 3.0 millimoles (mm), 0.77 gms, of rhodium dicarbonylacetylacetonate (Rh(CO)$_2$AcAc), 10 millimoles (mmol) of distilled 2-hydroxypyridine and 0.5 mmol of the specified alkali metal acetate salt or 0.25 mmol of the specified divalent metal acetate salt depending on the particular example. The reactor was sealed and charged with a gaseous mixture, containing equal molar amounts of carbon monoxide and hydrogen, to a pressure of 8,000 pounds per square inch (psig). Heat was applied to the reactor and its contents, when the temperature of the mixture inside the reactor reached 190°C, as measured by a suitably placed thermocouple, an additional adjustment of carbon monoxide and hydrogen ($H_2$:CO=1:1 mole ratio) was made to bring the pressure back to 8000 psig. The temperature was maintained at 220°C for 4 hours. During this period of time additional carbon monoxide and hydrogen was added whenever the pressure inside the reactor dropped below about 7500 psig. In a very reactive system where a large pressure drop is usually experienced, for instance where cesium was the cation, additional gas was added about every 15 minutes. With these added repressurizations the pressure inside the reactor was maintained at 8000 psig ± 400 psig over the entire 4 hours period.

After the 4 hour period, the vessel and its contents was cooled to room temperature, the excess gas vented and the reaction product mixture was removed. Analysis of the reaction product mixture was made by gas chromatographic analysis using a Hewlitt Packard FM model 810 Research Chromatograph, equipped with a 6 foot × ⅛ inch stainless steel column which contained a packing of John Mansville's CHROMOSORB 101. The gas chromatograph was held at 50° for 2 minutes after introduction of two microliters of product sample and then programmed from 50° to 280°C at 15°C per minute. The product analysis is reported for each example in the Table. The same equipment and procedure used in example 1 through 9 was used in examples 10 through 51 except for the reactants and conditions specified therein.

In examples 22 through 37 of Tables III and IV, the weight percent of rhodium initially charged to the reactor that was soluble in the reaction mixture after the reaction, was determined by atomic absorption analysis of the reaction mixture after the four hours of reaction time had lapsed and the unreacted gases were vented to the atmosphere. Atomic absorption analysis was run using a Perkin and Elmer Model 303 Atomic Absorption Spectrophotometer, sold by Perkin and Elmer of Norwalk, Conn.

TABLE I*

| Example | Promoter | $H_2O$ | Methanol | Methyl Formate | Ethanol | Ethylene Glycol | Glycol*** Formate | Glycerine |
|---|---|---|---|---|---|---|---|---|
| 1 | None | .13 | 2.11 | .15 | .02 | 1.0 | .03 | N.D.* |
| 2 | lithium acetate | .17 | 1.72 | .13 | .03 | 1.65 | .06 | N.D. |
| 3 | sodium acetate | .22 | 1.34 | .10 | .03 | 2.57 | .11 | N.D. |
| 4 | potassium acetate | .18 | .89 | .05 | .03 | 2.15 | .07 | N.D. |
| 5 | rubidium acetate | .32 | 3.59 | .31 | .04 | 2.24 | .11 | N.D. |
| 6 | cesium acetate | .28 | 1.58 | .14 | .04 | 3.90 | .20 | .25 |
| 7 | magnesium acetate | .15 | 1.33 | .09 | .05 | .70 | N.D. | N.D. |
| 8 | strontium acetate | .15 | 1.18 | .06 | .05 | .75 | N.D. | N.D. |
| 9 | barium acetate | .19 | .70 | .03 | .04 | .65 | N.D. | N.D. |

*All runs at 8000 psig. 1/1 H$_2$/CO, 220°C, 4 hr. 75cc dimethylether of tetraethylene glycol, 3.0 mm Rh(CO)$_2$ AcAc, 10.0mm distilled 2-hydroxypyridine, 0.45–0.50 milliequivalents of promoter
**N.D. - not detected in analysis of product.
***Glycol monoformate

TABLE II*

| Example | Promoter | H₂O | Methanol | Methyl Formate | Ethanol | Ethylene Glycol | Glycol** Formate | Glycerine |
|---|---|---|---|---|---|---|---|---|
| 10 | sodium fluoride | .22 | .90 | .05 | .02 | 1.56 | N.D. | N.D. |
| 11 | sodium chloride | .10 | 1.69 | .13 | .05 | 2.28 | .05 | N.D. |
| 12 | sodium bromide | .14 | 1.34 | .09 | .11 | 2.12 | .06 | N.D. |
| 13 | sodium iodide | N.D.*** | .46 | N.D. | .09 | .45 | N.D. | N.D. |
| 14 | cesium fluoride | .21 | 1.48 | .14 | .03 | 4.10 | .18 | N.D. |
| 15 | cesium chloride | .15 | 1.91 | .18 | .06 | 3.55 | .14 | N.D. |
| 16 | cesium bromide | N.D. | 1.69 | .14 | .10 | 2.60 | .08 | N.D. |
| 17 | cesium iodide | .21 | 1.74 | .11 | .17 | 1.80 | .06 | N.D. |
| 18 | cesium formate | .33 | 1.66 | .14 | .05 | 4.25 | .18 | .05 |
| 19 | cesium acetate | .28 | 1.58 | .15 | .04 | 3.90 | .20 | .25 |
| 20 | cesium pyridinolate | .20 | 1.70 | .14 | .05 | 4.35 | .20 | .25 |
| 21 | cesium sulfate | .27 | 1.55 | .10 | .02 | 1.44 | .05 | N.D. |

*All Runs at 8000 psig. 1/1 H₂/CO, 220°C, 4 hr. 75cc dimethylether of tetraethylene glycol, 3.0 mm Rh(CO)₂AcAc, 10.0 distilled 2-hydroxypyridine, 0.45–0.50 milliequivalents
**Glycol monoformate
***N.D. - not detected in analysis of product.

TABLE III*

| Example | Cesium Formate, mm. | Cs/Rh₆,mm | Wt.%** Soluble Rhodium | H₂O | Methanol | Methyl Formate | Ethanol | Ethylene Glycol | Glycol Mono-Formate | Glycerine |
|---|---|---|---|---|---|---|---|---|---|---|
| 22 | 0 | 0 | 67.9 | .20 | 2.00 | .13 | .02 | 1.00 | .01 | N.D. |
| 23 | 0.25 | 0.50 | 77.0 | .20 | 2.39 | .19 | .04 | 2.35 | .08 | N.D. |
| 24 | 0.33 | 0.66 | 78.0 | .27 | 1.88 | .14 | .04 | 3.25 | .12 | N.D. |
| 25 | 0.50 | 1.0 | 92.6 | .33 | 1.66 | .15 | .05 | 4.25 | .08 | .05 |
| 26 | 0.75 | 1.5 | 84.1 | .42 | 4.30 | .35 | .04 | 1.15 | .05 | N.D. |
| 27 | 1.0 | 2.0 | 89.6 | .25 | 5.92 | .54 | .04 | .55 | .03 | N.D. |
| 28 | 2.0 | 4.0 | 77.0 | .25 | 6.41 | .55 | .07 | .25 | N.D.*** | N.D. |
| 29 | 3.0 | 6.0 | 27.5 | .16 | .86 | .07 | .02 | .10 | N.D. | N.D. |

*All runs at 8000 psig, 1/1 H₂/CO, 4 hr., 75cc tetraglyme, 3.0mm Rh(CO)₂AcAc, 10.0mm distilled 2-hydroxy pyridine.
**Weight percent soluble rhodium base on total rhodium charged, in the reaction mixture at the end of 4 hour reaction time.
***N.D. - not detected in analysis.

TABLE IV*

| Example | Cesium Salt,mm** | Cs/Rh₆, moles | Wt.%*** Soluble Rhodium | H₂O | Methanol | Methyl Formate | Ethanol | Ethylene Glycol | Glycol** Formate | Glycerine |
|---|---|---|---|---|---|---|---|---|---|---|
| 30 | 0 | N.D.**** | 61.4 | .21 | 1.02 | .04 | N.D. | .50 | N.D. | N.D. |
| 31 | 0.33 | 0.50 | 80.0 | .19 | 1.60 | .08 | .03 | .40 | N.D. | N.D. |
| 32 | 0.44 | 0.67 | 89.1 | .20 | 1.62 | .09 | .04 | .60 | N.D. | N.D. |
| 33 | 0.67 | 1.0 | 95.9 | .38 | 1.30 | .09 | .05 | 2.00 | .06 | N.D. |
| 34 | 1.0 | 1.5 | 81.6 | .21 | 2.12 | .14 | .05 | 1.55 | .05 | .01 |
| 35 | 1.34 | 2.0 | 102 | .67 | 3.49 | .21 | .05 | .50 | N.D. | N.D. |
| 36 | 2.68 | 4.1 | 77.2 | .35 | 5.38 | .35 | .07 | .25 | N.D. | N.D. |
| 37 | 4.0 | 6.0 | 35.4 | .20 | .94 | .08 | .02 | N.D. | N.D. | N.D. |

*All runs at 6000 psig,1/1 H₂/CO, 220°C, 4 hrs, 100cc tetraglyme, 4.0mm Rh(CO)₂ AcAc, 13.5 mm distilled 2-hydroxy pyridine.
**Cesium 2-pyridinolate salt
***Weight percent soluble rhodium based on total rhodium charged in the reaction mixture at the end of 4 hour reaction time.
****N.D. - not detected in analysis.
*****Glycol monoformate

TABLE V*

| Example | Temp °C. | Cation,mm** | Rhodium,mm*** | Ligand,mm.**** | Methanol | Ethylene Glycol |
|---|---|---|---|---|---|---|
| 38 | 210 | 0.5 | 3.0 | 10.5 | 1.3 | 1.4 |
| 39 | 220 | 0.5 | 3.0 | 10.5 | 1.8 | 1.9 |
| 40 | 230 | 0.5 | 3.0 | 10.5 | 2.5 | 3.2 |
| 41 | 240 | 0.5 | 3.0 | 10.5 | 3.5 | 4.2 |
| 42 | 250 | 0.5 | 3.0 | 10.5 | 4.2 | 5.0 |
| 43 | 240 | 1.0 | 6.0 | 21 | 7.1 | 3.8 |
| 44 | 240 | 0.5 | 1.5 | 0.5 | 1.1 | 2.9 |
| 45 | 240 | 0.8 | 4.5 | 15.0 | 3.3 | 3.7 |
| 46 | 240 | 1.0 | 6.0 | 20 | 4.3 | 3.3 |

*All runs at 8000,psig., 1/1 H₂/CO, 4 hr. reaction time, and 75cc. of γ-butyrolactone as solvent.
**Millimoles of cesium 2-pyridinolate.
***Millimoles of rhodium dicarbonyl acetylacetonate
****Millimoles of 2-hydroxy pyridine.

EXAMPLE 47

Example 25 of Table III was repeated except that cesium 2-pyridinolate was used instead of cesium formate and the 2-hydroxypyridine ligand was omitted. Analysis of the product showed 0.68 grams methanol and 2.40 grams ethylene glycol.

EXAMPLE 48

Example 47 was repeated except that 0.6 moles of cesium 2-pyridinolate was charged to the reactor for every six moles of rhodium charged to the reactor. Analysis of this product showed 1.20 grams methanol and 0.5 grams ethylene glycol.

EXAMPLE 49

Example 48 was repeated except that 1.6 moles of cesium 2-pyridinolate was charged to the reactor for every six moles of rhodium charged to the reactor. Analysis of the product showed 3.51 grams methanol and 1.80 grams ethylene glycol.

EXAMPLE 50

Example 47 of Table III was repeated except that 10.0 mmol. of 8-hydroxyquinoline was added to the initial charge of reactants. Analysis of the products showed 2.92 grams of ethylene glycol and 1.64 grams of methanol.

EXAMPLE 51

Example 50 was repeated except that the 0.5 mmol. of cesium 2-pyridinolate was omitted. Analysis of products showed 0.35 grams of glycol and 1.57 grams of methanol.

What is claimed is:

1. In the process of making alkane polyols, which comprises reacting at a pressure of from about 500 psia to about 15,000 psia and a temperature of about 100°C to about 375°C, a mixture consisting essentially of oxides of carbon and hydrogen in the presence of an alkali metal cation and a rhodium carbonyl complex, said complex is provided to the reaction as a rhodium carbonyl cluster which possesses an infrared spectrum which exhibits three intense wavelength bands between about plus and minus 10 $cm^{-1}$ of about 1868 $cm^{-1}$, about 1838 $cm^{-1}$, and about 1785 $cm^{-1}$ at a pressure of at least about 500 psi, wherein the improvement comprises providing to the reaction mixture about 0.5 to about 1.5 atoms of the alkali metal cation for every six atoms of rhodium present in the reaction mixture.

2. The process of claim 1 wherein the alkali metal cation is present in about 0.75 to about 1.25 atoms of cation per every six atoms of rhodium.

3. The process of claim 2 wherein the alkali metal cation is present in about 1 atom of cation per every six atoms of rhodium.

4. The process of claim 1 wherein the cation is cesium.

5. The process of claim 1 wherein the reaction is effected in the presence of an inert solvent.

6. The process of claim 5 wherein the solvent is a dialkyl ether of alkylene glycols or polyalkylene glycol.

7. The process of claim 6 wherein the solvent is the dimethylether of tetraethylene glycol.

8. The process of claim 1 wherein the temperature of the reaction is from about 100°C. to about 375°C.

9. The process of claim 8 wherein the temperature of the reaction is from about 150°C. to about 300°C.

10. The process of claim 9 wherein the temperature of the reaction is from about 190°C. to about 275°C.

11. The process of claim 10 wherein the temperature of the reaction is from about 190°C. to about 240°C.

12. The process of claim 1 wherein the reaction is conducted under a pressure ranging from about 2,000 pounds per square inch absolute to about 12,000 pounds per square inch absolute.

* * * * *

UNITED STATES PATENT OFFICE
CERTIFICATE OF CORRECTION

Patent No. 3,952,039                    Dated April 20, 1976

Inventor(s)   Wellington E. Walker, David R. Bryant and Earle S. Brown

It is certified that error appears in the above-identified patent and that said Letters Patent are hereby corrected as shown below:

Column 4, line 64,

"or" should read -- for --.

Column 4, line 66,

"lest" should read -- least --.

Column 5, line 34,

"(N   )," should read -- (N≡), --.

UNITED STATES PATENT OFFICE
CERTIFICATE OF CORRECTION

Patent No. 3,952,039      Dated April 20, 1976

Inventor(s) Wellington E. Walker, David R. Bryant and Earle S. Brown

It is certified that error appears in the above-identified patent and that said Letters Patent are hereby corrected as shown below:

Columns 11 and 12, Table I
under sub-heading "Glycerine"

"ND*" should read  -- ND** --.

Signed and Sealed this

Eighth Day of November 1977

[SEAL]

Attest:

RUTH C. MASON
*Attesting Officer*

LUTRELLE F. PARKER
*Acting Commissioner of Patents and Trademarks*